(12) United States Patent
Colas et al.

(10) Patent No.: US 6,846,508 B1
(45) Date of Patent: Jan. 25, 2005

(54) METHOD FOR ADHERING SUBSTRATES USING ADHESIVE DEVICES CONTAINING SILICONE GELS

(75) Inventors: Andre Rudolf Louis Colas, Valbonne (FR); Gary Lord, Roquefort les Pins (FR); Marie Therese Valencia, Pegomas (FR); Xavier Thomas, Antibes (FR)

(73) Assignee: Dow Corning France, S.A., Valbonne (FR)

( * ) Notice: Subject to any disclaimer, the term of this patent is extended or adjusted under 35 U.S.C. 154(b) by 0 days.

(21) Appl. No.: 09/304,393

(22) Filed: May 4, 1999

(30) Foreign Application Priority Data

Jun. 5, 1998 (EP) .............................. 98480031

(51) Int. Cl.⁷ .............................. A61L 27/00; C09J 7/02
(52) U.S. Cl. ...................... 427/2.31; 427/2.1; 427/208; 428/447; 428/452; 428/355 R; 623/11; 442/151; 442/327; 604/307; 604/308
(58) Field of Search ................................. 428/447, 452, 428/355 R; 442/151, 327; 427/2.1, 2.31, 208; 623/11; 604/307, 308

(56) References Cited

U.S. PATENT DOCUMENTS

| 4,621,029 A | | 11/1986 | Kawaguchi | 428/447 |
| 4,832,978 A | * | 5/1989 | Lesser | 427/2 |
| 4,838,253 A | * | 6/1989 | Brassington et al. | 128/156 |
| 4,921,704 A | | 5/1990 | Fabo | 424/446 |
| 4,991,574 A | * | 2/1991 | Pocknell | 128/156 |
| 5,094,876 A | * | 3/1992 | Goldberg et al. | 427/2 |

FOREIGN PATENT DOCUMENTS

| CA | 638004 | 3/1962 | |
| CA | 2101509 | 1/1995 | |
| EP | 0308216 | 3/1989 | C09J/7/02 |
| EP | 0300620 B1 | 6/1992 | A61L/15/26 |
| EP | 0322118 B1 | 6/1992 | C08L/83/07 |
| GB | 2205243 A | 12/1988 | A61F/13/00 |
| GB | 2 192 142 | 11/1990 | |
| JP | 62155855 | 7/1987 | |
| JP | 10095072 | 4/1998 | B23B/27/00 |
| WO | WO 8600532 | 1/1986 | A61L/15/06 |
| WO | 96/09076 | 5/1992 | |
| WO | 93/19709 | 10/1993 | A61F/13/02 |
| WO | 93/19710 | 10/1993 | A61F/13/02 |
| WO | WO9424964 | 11/1994 | A61F/2/52 |
| WO | 95/22997 | 8/1995 | A61L/15/00 |
| WO | 96/29374 | 9/1996 | C09J/133/00 |

* cited by examiner

Primary Examiner—Daniel Zirker
(74) Attorney, Agent, or Firm—Roger E. Gobrogge

(57) ABSTRACT

A method for adhering a first substrate to a second substrate using a double sided adhesive device based on silicone gels. The method is particularly useful for adhering a medical prosthesis to a human or animal body.

7 Claims, No Drawings

METHOD FOR ADHERING SUBSTRATES USING ADHESIVE DEVICES CONTAINING SILICONE GELS

BACKGROUND OF THE INVENTION

The present invention relates to the use of a double sided adhesive device comprising silicone gels for adhering substrates, especially a medical prosthesis to a human or animal body.

Silicone pressure sensitive adhesives (PSAs) and tapes containing such adhesives are known in the art and many are commercially available. Typically, silicone PSAs comprise condensed blends of silicone fluids and silicone resins. When used as tapes, typically such silicone PSAs are applied as thin coatings (e.g., <0.1 mm) on one or both sides of a carrier material.

It is likewise known in the art to use silicone PSAs in medical applications. For instance, it is known to use silicone PSAs to adhere transdermal drug delivery devices and medical prosthesis to patients.

Silicone PSAs, however, can have a number of properties which limit their use in medical applications. For instance, the adhesive strength of silicone PSAs is often so great that a patient's skin or the object to be adhered can be damaged on removal of the PSA. Additionally, silicone PSAs often exhibit cold flow properties at skin temperature. As such, the resultant inflexible layers of PSA can be very uncomfortable on the patient's body. Finally, silicone PSAs often delaminate from the carrier leaving a coating of the PSA on the skin and/or the object to be adhered. Not only is this a cosmetic problem, but it also limits the ability to reuse the adhesive.

Silicone gels are also known in the art and described, for instance, in WO95/22997, WO96/09076 and EP300,620. These gels have been used, for example, as dielectrics, vibration dampers and in medical therapy for cutaneous scars or injuries (e.g., abrasions, surgical areas or burns). In this latter use, the silicone gel is in the form of a sheet with one tacky surface for adherence to the patient's skin and one non-tacky surface to inhibit undesirable adhesion to the gel (e.g., the patient's clothing).

We have now discovered an adhesive device comprising silicone gels which can be used, among other things, to provide a comfortable and convenient method for adhering a medical prosthesis to a human or animal body.

SUMMARY OF THE INVENTION

Accordingly, in one of its aspects the present invention provides a method for adhering a first substrate to a second substrate with an adhesive device, the improvement comprising the use of an adhesive device comprising:
  a carrier sheet, said carrier sheet having at least two surfaces;
  on one surface of the carrier sheet is a first, continuous layer of a silicone gel having a density in the range of about 100 to 4500 g/m$^2$; said gel having sufficient tack to adhere to the first substrate; and
  on a second surface of the carrier sheet is a second continuous layer of a silicone gel having a density in the range of about 100 to 4500 g/m$^2$, said gel having sufficient tack to adhere to the second substrate.

In another of its aspects, the present invention provides a substrate having an adhesive device for adhering it to a second substrate comprising:
  a substrate having a surface to be adhered to a second substrate; and
  on the surface of the substrate to be adhered to the second substrate, an adhesive device comprising:
  a carrier sheet, said carrier sheet having at least two surfaces;
  on one surface of the carrier sheet is a first, continuous layer of a silicone gel having a density in the range of about 100 to 4500 g/m$^2$; said gel having sufficient tack to adhere to the substrate; and
  on a second surface of the carrier sheet is a second continuous layer of a silicone gel having a density in the range of about 100 to 4500 g/m$^2$, said gel having sufficient tack to adhere to the second substrate,
  wherein the first continuous layer of silicone gel of the adhesive device is adhered to the surface of the substrate to be adhered to a second substrate.

In yet another of its aspects, the present invention provides a method for adhering a prosthesis to a human or an animal body comprising:
  positioning an adhesive device between the prosthesis and the human or animal body; and
  compressing the adhesive device between the prosthesis and the human or animal body, wherein the adhesive device comprises:
  a carrier sheet, said carrier sheet having at least two surfaces;
  on one surface of the carrier sheet is a first, continuous layer of a silicone gel having a density in the range of about 100 to 4500 g/m$^2$; said gel having sufficient tack to adhere to the prosthesis; and
  on a second surface of the carrier sheet is a second continuous layer of a silicone gel having a density in the range of about 100 to 4500 g/m$^2$, said gel having sufficient tack to adhere to the human or animal body.

The adhesion and physical properties of the adhesive devices used in the present invention can be tailored to specific end uses by modifying the gels.

In one preferred embodiment of the invention, one layer of gel in the adhesive device used in the present invention is sufficiently tacky to adhere to a human or animal body during its intended use and yet has sufficiently low tack to allow removal without discomfort. The second layer of gel in the adhesive device is sufficiently tacky to adhere to a medical prosthesis during its intended use and yet has sufficiently low tack to allow removal without damage. Because of this ease in removability and because the gel generally maintains its tack after removal, the devices of the invention can be reused. In addition, the reusability allows for easy and comfortable repositioning of medical prosthesis. Finally, silicone gels lack cold flow and, as such, are sufficiently soft to allow comfortable use by the human or animal.

DETAILED DESCRIPTION OF THE INVENTION

In its most generic form, the adhesive device used in the present invention comprises a carrier sheet having continuous layers of silicone gel on two surfaces. The gel layers can be designed to adhere to many substrates including medical prosthesis and human or animal bodies, hereafter 'animal bodies' or 'patients'.

The carrier sheet of the adhesive device used in the present invention serves as support and reinforcement for the silicone gel. Such carrier sheets generally comprise thin, coherent materials. They can be continuous or they can have perforations such as holes, gaps, or spaces therein. Preferred materials comprise non-woven materials.

Suitable materials to be used as the carrier sheets are known in the art for other purposes and are commercially available. Representative examples include soft plastic films such as polyethylene, polyamide, polyurethane, nylon, polyester, polypropylene, polytetrafluoroethylene, silicones and the like and non-woven polysaccharide based materials.

The carrier sheets should be chosen for the desired application of the adhesive device. If used for adhering prosthesis to patients, the carrier sheet is generally sufficiently thin and pliable to allow for comfortable wear by the patient while retaining sufficient strength to insure integrity of the gel during use. Generally, the carrier sheet has a density of about 5 to 150 g/m$^2$ which generally corresponds to a thickness in the range of about 0.01 to about 1 mm. Preferably, the carrier sheet has a density of about 10 to 50 g/m$^2$.

The silicone gel layers of the adhesive device used in the present invention should be chosen for the desired application of the adhesive device. If desired, different silicone gels can be used on each side of the carrier sheet such that the adhesion of the gels may vary.

If used for adhering prosthesis to patients, the gels should have sufficient tack to adhere to the body of the patient and to the prosthesis. The silicone gel should also be soft so that it is comfortable for the user and non-friable so that it is durable for its intended use.

The gels of the adhesive device used in the present invention are generally formed from linear or branched silicones having reactive groups thereon, as is known in the art. Such reactive groups undergo a crosslinking reaction during curing. Examples of crosslinking reactions include the hydrosilylation reaction in which a silicone having an Si-H reactive group reacts with a silicone having an aliphatically unsaturated reactive group in the presence of a platinum or rhodium catalyst. Alternatively, the reaction can involve the reaction of a silicone having an Si-OH reactive group with a silicone or a chain extender (e.g., a silane) having an alkoxy reactive group in the presence of a metal catalyst. In yet another alternative embodiment, a silicone having an Si-OH containing polymer is mixed with an alkoxysilane in the presence of a titanate catalyst. Other known cure mechanisms are also effective herein.

The preferred gels herein are obtained by reacting an alkenyl-substituted polydiorganosiloxane, preferably a polydimethylsiloxane having silicon-bonded vinyl, allyl or hexenyl groups, an organosiloxane containing silicon-bonded hydrogen atoms and a catalyst for the reaction of the SiH groups with the Si-alkenyl groups, such as a platinum metal or compounds or complexes thereof. Such compositions cure at normal ambient temperatures, but curing can be expedited by exposure to elevated temperatures, e.g., from about 40° C. to about 120° C.

Preferred Si-H and Si-alkenyl siloxanes to be used in the above reaction have viscosities in the range of 5 to 60,000 mm$^2$/second. The preferred ratio of (H as SiH)/(Alkenyl as Si-Alkenyl) is generally in the range of 0.1 to 10:1.

If desired, other components can be included in the gels of the present invention including, but not limited to, fillers, pigments, low temperature cure inhibitors, additives for improving adhesion, pharmaceutical agents, cosmetic agents, resins, fluids or other materials conventionally used in gels. Suitable gels and gel forming compositions are described in, for example, G.B. Patents 849,885, 945,580 and 2,192,142, U.S. Pat. No. 3,020,260, and EP399,520, EP261,167, EP300,620 and EP322,118, which are incorporated herein by reference.

The consistency, strength and tackiness of the gel is determined by a number of factors including the ratio of reactive groups in the materials, the viscosity of the polymers, and the like. One skilled in the art would know how to adjust this ratio to obtain a product with the properties desired for a given use.

As measured by the Cone Penetration Test method based on ASTM D-217-88, preferred gels have a penetration of 50 to 300 mm with a cone category 1806–1 weighted 62.5 g.

Generally, the gels have a density in the range of about 100 to 4500 $\mu$m$^2$ with densities in the range of about 150 to 1200 g/m$^2$ being preferred. Such gels would generally have thicknesses in the range of about 0.2 to about 5 mm with gels of 0.2 to 1.5 mm being preferred.

The adhesive strength of the silicone gels should be sufficient to maintain adhesion for the desired use. If the adhesive device is used to adhere a prosthesis to a patient, the adhesive strength of the gel used against the patient's body should be sufficient to ensure that the prosthesis remains attached to the patient and yet not so strong that excessive numbers of skin cells are removed when the adhesive device is removed. When measured with a Probe Tack Tester, the tack is generally between 50 and 500 g, with tack in the range of 150 to 350 g being preferred. The adhesive strength of the silicone gel used against the prosthesis is not as critical as that for the other gel layer. It should, however, be sufficient to ensure that adhesion is maintained without causing damage to the prosthesis when removed. As mentioned above, this can be the same or a different gel than the gel used for adherence to the patient body. Adhesive strengths are generally in the same range as that for the gel used for adherence to the patient body.

Since it is desired to have the gel adhere more strongly to the carrier sheet than either the patient's body or the prosthesis, an additional adhesive or an adhesion promoter may be used, if necessary, to bond the gel to the carrier sheet.

The silicone gels should be sufficiently soft and flexible to ensure comfort to the user. However, since softness also generally results in weaker gels, these two factors should be considered in selection and formulation of the gel.

If desired, the surfaces of the gels to be adhered to the patient and the prosthesis can be covered or protected with a release liner prior to use. Suitable release liner materials are known in the art and can include, for instance, a plastic or multi-ply material such as a silicone, a fluorinated silicone, a fluorine polymer, polyethylene, a PVC or the like. Additionally, the release liner could be made from a wide variety of materials (e.g., paper) coated with a suitable release coating. Finally, the surface of the release coating can be smooth, embossed or in any other desirable form.

The adhesive device used in the present invention can be made by any desirable technique. One example comprises preforming the gel (e.g., as a sheet) and the carrier sheet by known procedures e.g. by molding, calendering or casting and then bringing them together. For example, the gel may be preformed (e.g., as a sheet) by casting and curing the gel-forming composition on a suitable substrate. The carrier sheet may be preformed by calendering and then the carrier sheet applied over the gel. The second layer of gel can then be applied over the other exposed surface of the carrier sheet. Alternatively, the procedure may be reversed and the gel applied over the carrier sheet followed by applying the second gel layer over the exposed surface of the carrier sheet. If necessary, an adhesive may be employed to hold the components together in the laminated configuration.

Another method of making the adhesive device of this invention comprises (1) applying a gel forming composition to a substrate, (2) curing the gel forming composition to form the gel, (3) applying a carrier sheet precursor composition on the exposed surface of the gel, (4) curing the carrier sheet precursor to form the carrier sheet, (s) applying a second gel forming composition on the exposed surface of the carrier sheet and (6) curing the second gel forming composition.

Yet another suitable method comprises (1) applying a carrier sheet precursor composition to a substrate, (2) curing the carrier sheet precursor to form the carrier sheet, (3) applying a gel forming composition on one or both surfaces of the carrier sheet, and (4) curing the gel forming composition to form the gel(s). Obviously, if the gel was only formed on one surface of the carrier sheet during previous steps, the second layer of gel must be formed by a similar process.

In the above processes, the carrier sheet precursor composition and the gel forming composition may be applied by techniques such as dipping, spraying, coating, bar coating, etc. If desired, the carrier sheet precursor composition and the gel forming composition can be used as a dispersion or solution in a volatile solvent such as a organic solvent, a low molecular weight silicone or other suitable solvent and, thereafter, the solvent can be evaporated. An alternative method comprising hot melt silicones could also be used.

The substrate used in the above processes can be any surface which will impart the desired configuration to the compositions. Thus, it may be a continuous belt onto which the carrier sheet precursor composition or the gel forming composition is spread. Depending on the consistency of the compositions, the substrate may have barriers at its edges to restrict the flow of the compositions until cure takes place.

When it is desired to carry out the manufacture of the adhesive device of this invention as a continuous process, it is generally preferred to preform the carrier sheet as a separate operation. The preformed carrier sheet is then brought into contact with the silicone gel forming composition which is thereafter cured. Thus, for example, the carrier sheet may be laid on the exposed surface of the gel forming composition supported on a suitable substrate, or, alternatively the gel-forming composition may be coated on to the preformed carrier sheet. The gel forming composition is then cured.

In a preferred embodiment of the invention, the substrate is a preformed blister package. As such, the process would comprise (1) depositing the gel forming composition into the blister packaging, (2) applying the carrier sheet on the gel forming composition, (3) applying the second gel forming composition on the exposed surface of the carrier sheet and (4) curing both gel forming compositions and (5) sealing the blister pack.

In this preferred embodiment, the blister pack can be any of the conventional blister packaging materials including, for example, polyvinyl chloride, polypropylene, polyethylene, polyester, paper or composites with or without suitable release coatings. The blister pack could be sealed with conventional materials including, for example, the release liners described above or foils.

The adhesive device used in the present invention can be any size and shape desired based on the final use. For instance, it can be circular, square or rectangular and it can vary from a few square centimeters to in excess of several hundred square cm.

The adhesive devices used in the present invention are useful in applications where the adhesion provided by a silicone gel is useful. This can include, for example, adherence which requires shock absorbence such as in electrical components or in transportation devices and in application which require non-rigid adherence such as in construction. The adhesive devices of this invention are, however, particularly adapted for adhering medical prosthesis on patients. Examples of such prosthesis include devices such as breast prosthesis, catheters, cannulas, drainage bags, uridomes, incontinence devices, pouches, false hairpieces (e.g., toupees), tubes, ostomy and related devices, and the like. In addition, however, the adhesive devices can be used to adhere items such as surgery drapes, facial masks, gloves, and the like.

The following Examples illustrate the invention. Unless otherwise indicated, all percentages are by weight and all viscosities are at 25° C.

EXAMPLE 1

An adhesive device of the present invention was made by dipping a strip of non-woven polypropylene into a gel forming composition. The gel forming composition was made by mixing a vinyl terminated polydimethylsiloxane, a poly(dimethyl,methylhydrogen)siloxane; a hydrogen terminated polydimethylsiloxane; and a platinum catalyst. The gel forming composition was then cured for 30 minutes at room temperature and 30 minutes at 100° C. The resultant adhesive device had 850 g/m$^2$ gel on each surface of the polypropylene.

75 cm$^2$ of the above adhesive device was used to adhere a 1 kg external breast prosthesis on a vertical plastic surface. The prosthesis was maintained for 48 hours.

EXAMPLE 2

Four adhesive devices of the invention were made by the method of Example 1, except that the gel forming composition and its method of application to the polypropylene differed as follows:

Sample 1—A strip of non-woven polypropylene was dipped into a gel forming composition. The gel forming composition was made by mixing a 50:50 mixture of Part A comprising 99.3% vinyl terminated polydimethylsiloxane and 0.7% platinum complex catalyst and Part B comprising 2% poly(dimethyl,methylhydrogen) siloxane and 98% vinyl terminated polydimethylsiloxane. The gel forming composition was then cured for 15 minutes at room temperature and 30 minutes at 100° C. The resultant adhesive device was again dipped in the same gel forming composition and then cured for 15 minutes at room temperature and 30 minutes at 100° C.

Sample 2—A strip of non-woven polypropylene was dipped into a gel forming composition. The gel forming composition was made by mixing a 50:50 mixture of Part A comprising 99.8% vinyl-terminated polydimethylsiloxane and 0.2% platinum complex catalyst and Part B comprising 0.1% poly(dimethyl,methylhydrogen) siloxane; 23.3% hydrogen-terminated polydimethylsiloxane; and 76.6% vinyl-terminated polydimethylsiloxane. The gel forming composition was then cured for 120 minutes at room temperature. The resultant adhesive device was again dipped into the same gel forming composition and then cured for 120 minutes at room temperature and 15 minutes at 100° C. The device was post cured for 60 minutes at 100° C.

Sample 3—A strip of non-woven polypropylene was dipped into a gel forming composition. The gel forming composition was made by mixing a 50:50 mixture of Part A comprising 99.8% vinyl-terminated polydimethylsiloxane and 0.2% platinum complex catalyst and Part B comprising 0.1% poly (dimethyl,methylhydrogen) siloxane; 23.3% hydrogen-terminated polydimethylsiloxane; and 76.6% vinyl-terminated polydimethylsiloxane. The gel forming composition was then cured for 120 minutes at room temperature. The resultant adhesive device was again dipped into the same gel forming composition and then cured for 120 minutes at room temperature and 15 minutes at 100° C.

Sample 4—A strip of non-woven polypropylene was coated with a gel forming composition by using a bar coater. The gel forming composition was made by mixing 83% vinyl-terminated polydimethylsiloxane, 0.1% platinum complex catalyst, 4% poly(dimethyl,methylhydrogen) siloxane and 13% vinyl functional polydimethylsiloxane. The gel forming composition was then cured for 90 minutes at 100° C.

The adhesive strength of these materials was measured by a peel test. This test involved a 180 degree peel of the samples from a rigid silicone rubber panel. A tensile machine was used to measure the amount of force necessary to peel the samples. The results are presented in Table 1.

TABLE 1

| Sample | Mean Force (N/cm$^2$) |
| --- | --- |
| 1 | 0.17 |
| 2 | 0.42 |
| 3 | 0.81 |
| 4 | 3.85 |

This Example demonstrates the wide variation in tack of silicone gels.

EXAMPLE 3

Five 100 g samples of different gel forming compositions were prepared, deposited in paper cups and cured.

Sample 1—The gel forming composition was made by mixing vinyl-terminated polydimethylsiloxane, platinum complex catalyst, and poly(dimethyl,methylhydrogen) siloxane.

Sample 2—The gel forming composition was made by mixing 52.3% vinyl-terminated polydimethylsiloxane, 0.04% platinum complex catalyst, 2.5% poly(dimethyl, methylhexenyl)siloxane, 16.1% of trimethoxysilylethyl terminated polydimethylsiloxane, 0.2% poly(dimethyl, methylhydrogen)siloxane, 2.5% hydrogen-terminated polydimethylsiloxane and 26.4% 20cSt polydimethylsiloxane.

Sample 3—The gel forming composition was made by mixing 55.1% vinyl-terminated polydimethylsiloxane, 0.04% platinum complex catalyst, 7.7% of trimethoxysilylethyl terminated polydimethylsiloxane, 0.3% poly(dimethyl, methylhydrogen)siloxane, 3.2% hydrogen-terminated polydimethylsiloxane and 33.6% 20cSt polydimethylsiloxane.

Sample 4—The gel forming composition was made by mixing 44% vinyl-terminated polydimethylsiloxane, 0.04% platinum complex catalyst, 4.4% poly(dimethyl, methylhexenyl)siloxane, 22.9% of trimethoxysilylethyl terminated polydimethylsiloxane, 0.1% poly(dimethyl, methylhydrogen)siloxane, 1.7% hydrogen-terminated polydimethylsiloxane and 26.9% 20cSt polydimethylsiloxane.

Sample 5—The gel forming composition was made by mixing 48.2% vinyl-terminated polydimethylsiloxane, 0.04% platinum complex catalyst, 4.8% poly(dimethyl, methylhexenyl)siloxane, 25.1% of trimethoxysilylethyl-terminated polydimethylsiloxane, 0.3% poly(dimethyl, methylhydrogen)siloxane, 1.8% hydrogen-terminated polydimethylsiloxane and 19.8% 20cSt polydimethylsiloxane.

The gel forming compositions were then cured for 60 minutes at 100° c.

The softness and elasticity of these materials was measured by a penetration-relaxation test with a texture analyzer. The softness of materials is obtained by measuring the penetration in mm of a probe driven into the material with a fixed force. The softness is characteristic of adhesiveness and flexibility of final adhesive devices. The elasticity is obtained by recording the reaction of material subjected a penetration test. The elasticity is characteristic of cohesiveness of the final adhesive device and its ability to be removed and repositioned without damage and leaving residue. The results are presented in Table 2.

TABLE 2

| Sample | Penetration (mm) | % Elasticity |
| --- | --- | --- |
| 1 | 200 | 70 |
| 2 | 136 | 52 |
| 3 | 138 | 74 |
| 4 | 205 | 16 |
| 5 | 88 | 71 |

This examples demonstrates the wide variation in properties of the silicone gels.

That which is claimed is:

1. In a method for adhering a prosthesis to a human or animal body with an adhesive device, the improvement comprising the use of an adhesive device comprising:

a carrier sheet, said carrier sheet having at least two surfaces;

on one surface of the carrier sheet is a first, continuous layer of a silicone gel having a density in the range of about 100 to 4500 g/m$^2$; said gel having sufficient tack to adhere to the prosthesis; and on a second surface of the carrier sheet is a second continuous layer of a silicone gel having a density in the range of about 100 to 4500 $\mu$m$^2$, said gel having sufficient tack to adhere to the human or animal body; and wherein the first and second continuous layers of silicone gel are formed by the reaction of a silicone having Si-H groups with a silicone having Si-aliphatically unsaturated groups in the presence of a platinum or rhodium catalyst.

2. The method according to claim 1 in which the carrier sheet is non-woven and continuous and is made from a material selected from the group consisting of polysaccharide based materials, polyethylene, polyamide, polyurethane, nylon, polyester, polypropylene, polytetrafluoroethylene, and silicone.

3. The method according to claim 1 in which the carrier sheet has a density of about 5 to '150 g/m$^2$ and a thickness in the range of about 0.01 to about 1 mm.

4. The method according to claim 1 in which the first and second continuous layers of silicone gel have a thickness in the range of about 0.2 to 5 mm.

5. The method according to claim 1 in which the first and second continuous layers of silicone gel are covered by release liners.

6. A prosthesis having an adhesive device for adhering it to a human or animal body comprising:

a prosthesis having a surface to be adhered to a human or animal body; and on the surface of the prosthesis to be adhered to the human or animal body, an adhesive device comprising:

a carrier sheet, said carrier sheet having at least two surfaces;

on one surface of the carrier sheet is a first, continuous layer of a silicone gel having a density in the range of about 100 to 4500 $g/m^2$; said gel having sufficient tack to adhere to the prosthesis; and on a second surface of the carrier sheet is a second continuous layer of a silicone gel having a density in the range of about 100 to 4500 $g/m^2$, said gel having sufficient tack to adhere to the human or animal body, wherein the first continuous layer of silicone gel of the adhesive device is adhered to the surface of the prosthesis to be adhered to a human or animal body; and wherein the first and second continuous layers of silicone gel are formed by the reaction of a silicone having Si-H groups with a silicone having Si-aliphatically unsaturated groups in the presence of a platinum or rhodium catalyst.

7. A method for adhering a prosthesis to a human or an animal body comprising:

positioning an adhesive device between the prosthesis and the human or animal body; and compressing the adhesive device between the prosthesis and the human or animal body, wherein the adhesive device comprises:

a carrier sheet, said carrier sheet having at least two surfaces;

on one surface of the carrier sheet is a first, continuous layer of a silicone gel having a density in the range of about 100 to 4500 $g/m^2$; said gel having sufficient tack to adhere to the prosthesis; and on a second surface of the carrier sheet is a second continuous layer of a silicone gel having a density in the range of about 100 to 4500 $g/m^2$, said gel having sufficient tack to adhere to the human or animal body; and wherein the first and second continuous layers of silicone gel are formed by the reaction of a silicone having Si-H groups with a silicone having Si-aliphatically unsaturated groups in the presence of a platinum or rhodium catalyst.

* * * * *